(12) United States Patent
Fan et al.

(10) Patent No.: US 10,769,471 B2
(45) Date of Patent: Sep. 8, 2020

(54) SYSTEM AND METHOD FOR HOLDING AN IMAGE DISPLAY APPARATUS

(71) Applicant: KARL STORZ SE & Co. KG, Tuttlingen (DE)

(72) Inventors: Chunman Fan, Tuttlingen (DE); Johannes Fallert, Tuttlingen (DE); Yaokun Zhang, Tuttlingen (DE); Thorsten Ahrens, Tuttlingen (DE); Sebastian Wagner, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 16/590,683

(22) Filed: Oct. 2, 2019

(65) Prior Publication Data

US 2020/0110956 A1 Apr. 9, 2020

(30) Foreign Application Priority Data

Oct. 3, 2018 (DE) .......................... 10 2018 124 432

(51) Int. Cl.
*G09G 5/00* (2006.01)
*G06K 9/32* (2006.01)
(Continued)

(52) U.S. Cl.
CPC ........ *G06K 9/3208* (2013.01); *A61B 1/00006* (2013.01); *A61B 1/00009* (2013.01);
(Continued)

(58) Field of Classification Search
CPC . A61B 90/37; A61B 1/00006; A61B 1/00009; A61B 1/00045; A61B 1/00147;
(Continued)

(56) References Cited

U.S. PATENT DOCUMENTS 6,471,637 B1 10/2002 Chatenever et al.
7,382,399 B1 * 6/2008 McCall ................ H04N 5/2254
348/207.99
(Continued)

FOREIGN PATENT DOCUMENTS

DE 102008057734 A1 5/2010
EP 0712289 B1 5/1997
(Continued)

OTHER PUBLICATIONS

German Search Report for corresponding German Patent Application No. 10 2018 124 432.0, dated May 8, 2019.
(Continued)

*Primary Examiner* — Howard D Brown, Jr.
(74) *Attorney, Agent, or Firm* — Jason H. Vick; Sheridan Ross, PC

(57) ABSTRACT

A system for holding an image display apparatus (60) for displaying an image captured by means of an image capturing apparatus (20) comprises a movable holding apparatus (70) for an alterable hold of the image display apparatus (60), a controllable drive device (72) for moving the holding apparatus (70), comprising a control signal input (74) for receiving a control signal, and a controller (40) comprising a signal input (42) for receiving a signal that represents an orientation or a change in the orientation of the viewing direction (28) of the image capturing apparatus (20) in space or that facilitates a determination of the orientation or the change in the orientation of the viewing direction (28) of the image capturing apparatus (20), and comprising a control signal output (47), couplable to the control signal input (74) of the controllable drive device (72), for providing a control signal for controlling the controllable drive device (72). The controller (40) is embodied and provided to control the controllable drive device (72) in such a way that, within a predetermined range of possible orientations of the viewing (Continued)

direction (28) of the image capturing apparatus (20) in space, the orientation of the image display apparatus (60) in space is a predetermined function of the orientation of the viewing direction (28) of the image capturing apparatus (20) in space.

12 Claims, 6 Drawing Sheets

(51) Int. Cl.
*A61B 90/00* (2016.01)
*G06T 7/73* (2017.01)
*A61B 1/00* (2006.01)
*H04N 5/225* (2006.01)
*H04N 5/44* (2011.01)

(52) U.S. Cl.
CPC .......... *A61B 1/00045* (2013.01); *A61B 90/37* (2016.02); *G06T 7/73* (2017.01); *H04N 5/225* (2013.01); *H04N 5/4403* (2013.01); *A61B 2090/372* (2016.02); *G06T 2207/30244* (2013.01); *H04N 2005/2255* (2013.01); *H04N 2005/4408* (2013.01); *H04N 2005/4428* (2013.01)

(58) Field of Classification Search
CPC ............ A61B 1/00174; A61B 1/00043; A61B 2090/372; G06K 9/3208; G06T 7/73; G06T 2207/30244; H04N 5/225; H04N 5/4403; H04N 2005/2255; H04N 2005/4408; H04N 2005/4428

See application file for complete search history.

(56) References Cited

U.S. PATENT DOCUMENTS

| | | |
|---|---|---|
| 8,187,167 B2 | 5/2012 | Kim |
| 2002/0188172 A1 | 12/2002 | Irion et al. |
| 2007/0180129 A1 | 8/2007 | Tolmie et al. |
| 2010/0125166 A1 | 5/2010 | Henzler |
| 2011/0032220 A1* | 2/2011 | Shih ..................... G06K 9/3208 345/204 |
| 2012/0296164 A1 | 11/2012 | Kim |
| 2014/0320624 A1* | 10/2014 | Lee .................... H04N 21/4318 348/78 |
| 2018/0110569 A1* | 4/2018 | Drain .................... A61B 90/30 |

FOREIGN PATENT DOCUMENTS

| | | |
|---|---|---|
| EP | 2818118 A1 | 12/2014 |
| KR | 2015-0135752 | 12/2015 |
| WO | WO 95/01749 A1 | 1/1995 |
| WO | WO 98/46120 | 10/1998 |
| WO | WO 2006/046809 A1 | 5/2006 |

OTHER PUBLICATIONS

European Search Report for corresponding European Application No. 19201366.2, dated Feb. 26, 2020.

\* cited by examiner

SYSTEM AND METHOD FOR HOLDING AN IMAGE DISPLAY APPARATUS

CROSS REFERENCE TO RELATED APPLICATIONS

This application claims the benefit under 35 U.S.C. 119(a) to German Patent Application No. 10 2018 124 432.0, filed Oct. 3, 2018, the disclosure of which is incorporated herein by reference in its entirety.

SUMMARY

The present invention is directed to a system for holding an image display apparatus and to a method for displaying an image.

Within the scope of micro-invasive medical measures, the direct view through an endoscope is increasingly being replaced by a camera and displaying the image captured by the camera on one or more screens. This allows the medical staff to maintain an ergonomically more expedient and less tiring body posture. Further, a plurality of members of the medical team can simultaneously observe the medical measure on one or more screens. Further, the images of the medical measure can be recorded for documentation purposes and/or can be transmitted into a lecture hall, for example, for training purposes.

As a rule, the person guiding the endoscope directly by hand or controlling a motor-driven movement of the endoscope knows the position and orientation of the endoscope and its viewing direction at all times. All other parties involved have to resort to verbal notifications or their own observation of the movements of the displayed image and their own anatomical knowledge.

For assisting medical staff with finding their bearings in the displayed image, particularly with grasping the current orientation of the endoscope and the viewing direction in a manner that is as intuitive as possible, the suggestion of superimposing auxiliary objects into the image, said auxiliary objects indicating a predetermined and fixed reference direction, for example, has already arisen. Further, rotating or deforming the image displayed on the screen in a manner corresponding to the orientation of the endoscope has also already been proposed.

WO 95/01749 A1 (also published as EP 0 712 289 B1) has described an apparatus for rotating an image display device, facilitating an orientation of the displayed image that corresponds to the actual orientation (page 2, lines 20 to 26). The deflection electrodes of a cathode ray tube of a screen are arranged on a frame that can be rotated by means of a servomotor 22 (page 5, lines 26 to 33; FIG. 5).

U.S. Pat. No. 8,187,167 B2 (also published as WO 2006/046809 A1; similar: US 2012-0296164 A1) has described a display apparatus for laparoscopy. The display apparatus comprises a screen for reproducing an image captured by means of a laparoscope. The screen is rotatable in motor driven fashion about the surface normal of its image display surface. The display apparatus further comprises a foot switch, by means of which medical staff can control a rotation of the screen.

An object of the present invention consists of developing an improved system for holding an image display apparatus and an improved method for displaying an image captured by means of a movable image capturing apparatus (20).

This object is achieved by the subjects of the independent claims.

Developments are specified in the dependent claims.

Embodiments of the present invention are based on the concept of moving a screen, a monitor or any other image display apparatus that reproduces an image captured by means of an endoscope, an exoscope or any other image capturing apparatus, in such a way that the orientation of the image display apparatus in space corresponds or largely corresponds to, or at least indicates, the orientation of the image capturing apparatus in space at all times.

A system for holding an image display apparatus for displaying an image captured by means of an image capturing apparatus comprises a movable holding apparatus for the alterable hold of the image display apparatus, a controllable drive device for moving the holding apparatus, comprising a control signal input for receiving a control signal, and a controller comprising a signal input for receiving a signal that represents an orientation or a change in the orientation of the viewing direction of the image capturing apparatus in space or that facilitates a determination of the orientation or the change in the orientation of the viewing direction of the image capturing apparatus, and comprising a control signal output, couplable to the control signal input of the controllable drive device, for providing a control signal for controlling the controllable drive device, wherein the controller is embodied and provided to control the controllable drive device in such a way that, within a predetermined range of possible orientations of the viewing direction of the image capturing apparatus in space, the orientation of the image display apparatus in space is a predetermined function of the orientation of the viewing direction of the image capturing apparatus in space.

In particular, neither of the image capturing apparatus and the image display apparatus are constituent parts of the system. However, the system may alternatively comprise an image capturing apparatus and may be embodied and provided for the combination with an image display apparatus that is not a constituent part of the system; or said system may comprise an image display apparatus and may be embodied and provided for the combination with an image capturing apparatus that is not a constituent part of the system; or said system may comprise both an image capturing apparatus and an image display apparatus.

In particular, the image capturing apparatus is an endoscope, an exoscope, a surgical microscope or any other apparatus for capturing a monocular image or a stereoscopic image. The image capturing apparatus may comprise one or more cameras or one or more image sensors for capturing an image or a stereo image and for producing an image signal that represents the image or stereo image. Alternatively, the image capturing apparatus may be embodied and provided to be optically coupled to one or more cameras or one or more image sensors, for example by way of an eyepiece.

In particular, the image display apparatus comprises one (or more) screen(s) or monitor(s) or one (or more) projector (s) with one (or more) assigned projection surface(s).

The holding apparatus may be embodied and provided for a permanent connection, i.e., a connection that cannot be released in non-destructive fashion or that can only be released using tools, with an image display apparatus. Alternatively, the holding apparatus may be embodied and provided for an easily releasable connection, in particular also a connection that is releasable by medical staff and/or without the use of tools, with an image display apparatus.

The holding apparatus may have one or more rotational degrees of freedom and, optionally, one or more translational degrees of freedom. In particular, the holding apparatus comprises one or more joints for each rotational degree of freedom and one or more linear guides or linear bearings, which facilitate a telescopic property, for example, for each translational degree of freedom. Alternatively, a translational degree of freedom can be realized by means of one or more joints. These joints may facilitate rotational degrees of freedom, once again at the same time.

The movable holding apparatus may respectively comprise a joint defining a horizontal pivot axis or axis of rotation and a joint defining a vertical pivot axis or axis of rotation. In particular, the movable holding apparatus comprises a joint that defines a pivot axis or axis of rotation that is vertical at all times, a joint that defines a pivot axis or axis of rotation that is horizontal at all times, said axis being pivotable about the vertical pivot axis, and a joint that defines a third pivot axis that is orthogonal to the vertical first pivot axis at all times and orthogonal to the second pivot axis that is horizontal at all times.

Further, the movable holding apparatus may comprise a plurality of linear guides or linear bearings, which each define a straight or curved path. In this case, a first linear guide may have a stationary arrangement, with one or more further linear guides being movable along the path defined by the first linear guide. By way of example, a first linear guide of the holding apparatus may define a straight horizontal translation path and a second linear guide may define a straight vertical translation path.

Alternatively, the movable holding apparatus can be embodied in such a way that not all pivot axes or axes of rotation and translation paths, or only the pivot axes or axes of rotation and translational paths in individual configurations the holding apparatus, are oriented orthogonal to one another and either vertically (i.e., in the direction of gravity) or horizontally (i.e., orthogonal to the vertical). In particular, the holding apparatus may comprise one or more hexapods and/or have a similar embodiment to the apparatuses usually referred to as industrial robots. A hexapod and a configuration in the style of an industrial robot comprising a plurality of joints, which each define a pivot axis or an axis of rotation, are examples in which even translational degrees of freedom are implemented purely by joints.

The controllable drive device may be partly or completely integrated in the holding apparatus. The controllable drive device may comprise one or more electric, pneumatic, hydraulic or other motors or actuators and one or more transmissions. In particular, a motor or actuator is assigned to each degree of freedom of the movable holding apparatus.

The controller can be embodied and provided to process, in analog or digital, electric, optical or any other fashion, originally electric, optical or other analog or digital signals and to produce electric, optical or other analog or digital signals. A power supply for providing electric, pneumatic, hydraulic or any other power for one or more motors or actuators of the drive device may be integrated into the controller. Alternatively, the controller may only be embodied and provided to actuate one or more power supplies for electric motors or actuators or to actuate valves. The controller can also be integrated into the drive device and/or also be integrated into the holding apparatus.

In particular, the orientation the viewing direction of the image capturing apparatus or of the image display apparatus in space means the orientation of the apparatus in relation to any predetermined coordinate system. By way of example, a Cartesian coordinate system with two horizontal axes and one vertical axis may be considered as a coordinate system. The direction of the gravitational force acting at the location of the system is vertical; any direction orthogonal thereto is horizontal. By way of example, the horizontal axes of the coordinate system are tangents to the circles of latitude and longitude of the global spherical coordinate system at the Earth's surface. Alternatively, one or more axes of the coordinate system may be used parallel to the edges of a cuboid space in which the system is arranged or to the basic directions (e.g., dorsal-caudal and lateral) of a patient.

By way of example, the orientation of an apparatus in space can be described by the angle between reference directions of the apparatus and axes of the coordinate system or between reference directions of the apparatus and planes spanned by the axes of a coordinate system.

In particular, the viewing direction of the image capturing apparatus is a reference direction thereof. The direction of a straight edge portion of a rectangular image or image field of an image capturing apparatus can be used as a further reference direction of the image capturing apparatus. In the case of an image capturing apparatus that produces a circular image, for example like many endoscopes, a straight edge portion of a region that is captured by a camera coupled to the image capturing apparatus can be used.

The viewing direction of the image capturing apparatus is the direction from a light entry surface of the image capturing apparatus (at the distal end, in particular) to a very distant object that lies in the center of the field of view and that is consequently imaged in the center of the image field. In the case of an image sensor whose image signals are not used in the totality thereof, the viewing direction is the direction in which a very distant object lies, said object being imaged in the center of that region of the image sensor whose image signals are in fact transmitted and displayed on the image display apparatus. The viewing direction of an image capturing apparatus can be alterable, in particular pivotable, in relation to the image capturing apparatus, for example in the case of an endoscope with a pivoting prism or a pivotable camera at its distal end.

By way of example, the surface normal or—in the case of a curved image display surface—the central surface normal of the image display surface or the surface normal of the image display surface of an image display apparatus at the center thereof and a straight portion of a rectangular edge of the image display surface can be used as reference directions for the image display apparatus.

In particular, the orientation of an apparatus can be specified by an azimuth angle (also referred to as horizontal angle), a zenith angle (also referred to as elevation or, depending on the sign, as a height angle or depth angle) and a third angle (referred to as inclination angle below). The azimuth angle is measured within a horizontal plane in a certain direction (in particular in the clockwise sense as seen from above) from a certain direction (e.g., North). The zenith angle is measured as an angle with respect to the vertical. The elevation or the height angle is measured as an angle with respect to the horizontal plane; the term depth angle is also used in the case of a negative sign. By way of example, the orientation of an apparatus can be specified as azimuth angle, zenith angle and inclination angle of the apparatus in relation to a reference orientation of the apparatus.

The predetermined range of possible orientations of the image capturing apparatus in space, within which the orientation of the image display apparatus is a predetermined function of the orientation of the image capturing apparatus, can be a manifold with a dimension of 1, 2 or 3. By way of example, the image display apparatus may only be pivotable about a vertical pivot axis or axis of rotation, wherein the controller is embodied and provided to keep the direction of the central surface normal of the image display surface of the image display apparatus parallel within a certain angle range at all times to the projection of the viewing direction of the image capturing apparatus onto a horizontal plane. As an alternative or in addition thereto, the image display apparatus can be pivotable about a horizontal axis (in particular parallel to the image display surface of the image display apparatus or orthogonal to the central surface normal of the image display surface), wherein the controller is embodied and provided to move the image display apparatus within a predetermined angle range at all times such that the zenith angle for the viewing direction of the image capturing apparatus and the zenith angle for the central surface normal of the image display surface of the image display apparatus are the same.

Limits of the predetermined range of possible orientations of the image capturing apparatus within which the orientation of the image display apparatus is a predetermined function of the orientation of the viewing direction of the image capturing apparatus emerge, for example, from limits of the mobility of the image display apparatus. By way of example, for geometric reasons, hexapod only facilitates pivoting within a restricted solid angle range (the content of which, as a rule, is less than or not much greater than $2\pi$ (2 pi) but in most cases significantly less than $4\pi$ (4 pi)). Further, limits of the predetermined range may result from the length or elasticity of bending of cables on the image display apparatus and, in particular, from the requirement that medical staff should be able to observe without impairments the image displayed by the image display apparatus without having to change their location.

The system facilitates an intuitive grasp of the current orientation of the viewing direction of the image capturing apparatus by the user or observer purely on the basis of perceiving the orientation of the image display apparatus.

In a system as described here, the controller is embodied, in particular, to control the drive device in such a way that, within a predetermined angle range, pivoting of the viewing direction of the image capturing apparatus about a first axis causes pivoting of the image display apparatus about a second axis.

In particular, the controller is embodied to control the device drive in such a way that, within a predetermined angle range, any pivoting of the viewing direction of the image capturing apparatus about a first axis causes pivoting of the image display apparatus about a second axis.

In particular, the first axis is orthogonal or substantially orthogonal to the viewing direction of the image capturing apparatus. In particular, the second axis is orthogonal or substantially orthogonal to a surface normal or—in the case of a curved image display surface of the image display apparatus—to a central surface normal or to a surface normal of the image display surface of the image display apparatus.

The first axis and the second axis may be parallel or substantially parallel. In particular, the first axis is horizontal and orthogonal to the viewing direction of the image capturing apparatus. Alternatively, the first axis is, e.g., orthogonal to the viewing direction of the image capturing apparatus and orthogonal to a horizontal that, in turn, is orthogonal to the viewing direction. In particular, the first axis may be vertical.

In a system as described here, the controller is embodied, in particular, to control the drive device in such a way that, in respect of pivoting the viewing direction of the image capturing apparatus about the first axis and pivoting the image display apparatus about the second axis within the predetermined angle range, every angle position of the viewing direction of the image capturing apparatus is associated with an angle position of the image display apparatus.

The assignment can be defined by a mathematical function or by a table (often referred to as look-up table). The assignment between the angle position of the viewing direction of the image capturing apparatus and the angle position of the image display apparatus corresponds to a monotonic or strictly monotonic mathematical function, in particular.

The predetermined angle range and its limits can take account of boundary conditions such as the length or elasticity of a cable or the admissible pivoting range of a joint. Further, limits of the predetermined angle range may result from the requirement that medical staff should be able to observe without impairments the image displayed by the image display apparatus without having to change their location.

In particular, the assignment is such that, in the center or in a central region of the predetermined angle range, any pivoting of the image capturing apparatus through a small angle causes pivoting of the image display apparatus through the same angle. In particular, the assignment is such that the ratio between the angle through which the image display apparatus is pivoted to the angle through which the image capturing apparatus is pivoted becomes ever smaller toward the edges of the predetermined angle range. Thus, on the one hand, the orientation of the image display apparatus in space can precisely reproduce the orientation of the image capturing apparatus in space in the center of the predetermined angle range and, on the other hand, an observation of an image displayed by the image display apparatus can still be facilitated at the edges of the predetermined angle range.

In a system as described here, the controller is further embodied, in particular, to control the drive device in such a way that pivoting of the viewing direction of the image capturing apparatus about the first axis further causes a movement of the image display apparatus along a path.

In particular, the path is curved, for example in arcuate fashion. In particular, the path lies in a plane or substantially in a plane orthogonal to the second axis and/or to the first axis. The controller can be embodied to control the drive device in such a way that the image display apparatus is simultaneously pivoted about the second axis and moved along the path. The position of the path may, in turn, be dependent on an angle position of the viewing direction of the image capturing apparatus in relation to a further axis which, in particular, is orthogonal to the first axis. By way of example, the image display apparatus may be simultaneously pivotable about a horizontal axis and about a vertical axis and movable on a sphere surface or on a surface of an ellipsoid or on any other curved surface. Here, the controller is embodied, in particular, to control the drive device in such a way that the central surface normal of the image display surface of the image display apparatus always points at the center of curvature of the surface along which the image display apparatus is movable at the point at which the image display apparatus is currently situated. Expressed differently, the controller is embodied, in particular, to control the drive device in such a way that the image display surface of the image display apparatus is parallel at all times to the local tangential surface of the surface along which the image display apparatus is movable.

In a system as described here, the controller is further embodied, in particular, to control the drive device in such a way that, within the predetermined angle range, a position of the image display apparatus along the predetermined path is associated with each angle position of the viewing direction of the image capturing apparatus.

In a system as described here, the holding apparatus comprises, in particular, one or more joints that allow pivoting of the image display apparatus about the second axis, wherein the drive device comprises one or more motors or actuators for pivoting an image display apparatus, held by means of a holding apparatus, about the second axis.

In a system as described here, the controller is further embodied, in particular, to control the drive device in such a way that, within a predetermined angle range, altering an angle between the viewing direction of the image capturing apparatus and the vertical causes a change in the angle between the surface normal of an image display surface of the image display apparatus and the vertical.

In particular, the controller is embodied to control the drive device in such a way that, within a predetermined angle range, any alteration of an angle between the viewing direction of the image capturing apparatus and the vertical causes a change in the angle between the surface normal of an image display surface of the image display apparatus and the vertical.

In a system as described here, the controller is embodied, in particular, to control the drive device in such a way that, within a predetermined angle range, pivoting of the viewing direction of the image capturing apparatus, more particularly any pivoting of the viewing direction of the image capturing apparatus, about a first horizontal axis causes pivoting of the image display apparatus about a second horizontal axis.

In particular, the second horizontal axis is parallel to the first horizontal axis. In particular, the first horizontal axis is orthogonal to the viewing direction of the image capturing apparatus.

In a system as described here, the controller is embodied, in particular, to control the drive device in such a way that, within a predetermined angle range, an angle between the surface normal of the image display surface of the image display apparatus and the vertical is associated with each angle between the viewing direction of the image capturing apparatus and the vertical.

In a system as described here, the controller is further embodied, in particular, to control the drive device in such a way that pivoting of the viewing direction of the image capturing apparatus about the first horizontal axis further causes a movement of the image display apparatus along a path that is vertically or substantially vertically, at least in a small portion or at a point.

In particular, the path is arcuate or curved differently. In particular, the path lies in a vertical plane. In particular, the path lies in a vertical plane that is orthogonal to the first horizontal axis. In particular, the first horizontal axis is orthogonal to the viewing direction of the image capturing apparatus.

In a system as described here, the controller is embodied, in particular, to control the drive device in such a way that, within the predetermined angle range, a position of the image display apparatus along the predetermined path is associated with each angle position of the viewing direction of the image capturing apparatus.

In a system as described here, the controller is further embodied, in particular, to control the drive device in such a way that a translational movement of the image capturing apparatus causes a translational movement of the image display apparatus.

In a system as described here, the signal input of the controller is further embodied, in particular, to receive a signal that represents a position or a change in the position of the image capturing apparatus or that facilitates a determination of the position or the change in the position of the image capturing apparatus, wherein the controller is further embodied and provided to control the controllable drive device in such a way that, within a predetermined range of possible positions of the image capturing apparatus, the position of the image display apparatus is a predetermined function of the position of the image capturing apparatus.

The position of an apparatus means the position of a reference point of the apparatus, for example of the center point of the light entry surface of the image capturing apparatus or of the center point of the image display surface of the image display apparatus. Any rotation of an apparatus about its reference point does not change its position. A purely translational movement of the apparatus changes its position but not its orientation.

The predetermined region can be a manifold with one, two or three dimensions, in particular corresponding to the same number of degrees of freedom. The position of the image display apparatus may indicate the position of the image capturing apparatus such that medical staff can deduce the position of the image capturing apparatus from the position of the image display apparatus.

In a system as described here, the signal input of the controller is embodied, in particular, to receive from a sensor a signal or a signal that has been integrated over time.

The signal input of the controller is embodied and provided, in particular, to receive a signal from a sensor for capturing the direction of the gravitational force and/or for capturing a linear acceleration and/or for capturing a rotation and/or for capturing a direction and/or a strength of a magnetic field.

A system as described here further comprises, in particular, a sensor for capturing at least either the direction of the gravitational force or of a linear acceleration or a rotation or a direction or strength of a magnetic field.

A sensor for capturing a rotation comprises, in particular, a gyroscope, a vibrating structure gyroscope or any other rate sensor. In particular, the sensor is a constituent part of the image capturing apparatus or mechanically rigidly connected or connectable to the latter.

The orientation of an image capturing apparatus relative to the vertical can be determined by capturing the direction of the gravitational force by means of a sensor in or at the image capturing apparatus. By capturing the direction of the Earth's magnetic field or, for example, an artificially produced magnetic field in an operating theater by means of a sensor arranged in or at an image capturing apparatus, it is possible to determine the orientation of the image capturing apparatus relative to the magnetic field. By capturing the direction of an artificially produced electric field or by capturing the polarization of an alternating electromagnetic field by means of a sensor arranged in or at an image capturing apparatus, it is possible to determine the orientation of the image capturing apparatus relative to said field.

Proceeding from an initial position and an initial orientation, the position and orientation of the viewing direction of an image capturing apparatus can be calculated by twofold integration of the linear or translational acceleration captured by a sensor in or at the image capturing apparatus and by a single integration of the rotation rate.

In a system as described here, the signal input of the controller is embodied, in particular, to receive an image signal from a camera for capturing an operating field, wherein the controller is embodied and provided to determine the orientation of the image capturing apparatus by evaluating an image signal received at the signal input.

A system as described here further comprises, in particular, a camera for capturing an operating field and for producing an image signal, said camera being coupled to the signal input of the controller.

The camera for capturing the operating field should not be mixed up with the image capturing apparatus. In particular, the camera for capturing the operating field is arranged above or obliquely above or next to the operating field. The camera can be a stereo camera such that an evaluation of its stereo image allows information to be obtained about the orientation and the location (in all three dimensions) of the image capturing apparatus. The camera can be embodied and provided to capture an image in the wavelength range visible to the healthy human eye or in a part thereof and/or in one or more other wavelength ranges (e.g., infrared).

The controller can be provided to receive and evaluate image signals from a plurality of cameras. In particular, the controller is provided and embodied to identify a proximal end of an image capturing apparatus or a special marking at the proximal end of an image capturing apparatus. By capturing the position and, optionally, the size of the image of the proximal end of the image capturing apparatus, too, and possibly by comparing the images from a plurality of cameras, it is possible to determine the position and the orientation of the proximal end of the image capturing apparatus. From the position and orientation of the proximal end of a rigid image capturing apparatus, it is possible to calculate the position and orientation of the distal end of the image capturing apparatus and, in particular, the orientation of the viewing direction of the image capturing apparatus.

In a system as described here, the signal input of the controller is embodied, in particular, to receive a signal from a receiver for electromagnetic waves which emanate from the image capturing apparatus, wherein the controller is embodied and provided to determine the orientation of the image capturing apparatus in space by evaluating the signal received from the receiver.

A system as described here further comprises, in particular, a receiver for receiving electromagnetic waves emanating from the image capturing apparatus.

The image capturing apparatus may comprise one or more sensors for capturing the orientation of the image capturing apparatus or the viewing direction of the image capturing apparatus and a transmitter for emitting an electromagnetic wave or a transponder for diffusely reflecting a modified electromagnetic wave. The transmitter or transponder is embodied in such a way that the emitted electromagnetic wave or the modified, diffusely reflected electromagnetic wave contains information about the orientation of the image capturing apparatus and, optionally, about its position, too.

Alternatively, the image capturing apparatus may comprise one or more reflectors for reflecting electromagnetic waves and/or one or more transmitters for emitting electromagnetic waves, wherein the controller is embodied to deduce the orientation of the image capturing apparatus from the intensity or amplitude or power density and/or from the polarization and/or from the phase angle of one or more of the electromagnetic waves reflected or emitted by the image capturing apparatus and received by the receiver.

In particular, the receiver comprises an antenna or a plurality of antennas for receiving the electromagnetic wave. In particular, the frequency of the electromagnetic wave lies between several hundred kHz and a few GHz.

In a system as described here, the controller is embodied, in particular, to control the drive device in such a way that, within a predetermined angle range, a rotation of the image capturing apparatus through a first angle about its viewing direction causes a rotation of the image display apparatus through a second angle, wherein the second angle is a predetermined fraction of the first angle or a predetermined non-constant function of the first angle or a predetermined function of the angle position of the image capturing apparatus.

Alternatively, the controller can be embodied in such a way that the second angle equals the first angle.

In particular, the controller is embodied to control the drive device in such a way that, within a predetermined angle range, each rotation of the image capturing apparatus through a first angle about its viewing direction causes a rotation of the image display apparatus through a second angle.

In particular, the controller is embodied to control the drive device in such a way that, within a predetermined angle range, any or each rotation of the image capturing apparatus about its viewing direction causes a rotation of the image display apparatus about the central surface normal of the image display surface of the image display apparatus. In particular, the controller is embodied to control the drive device in such a way that a rotation of the image capturing apparatus in a direction of rotation (in relation to the viewing direction from the image capturing apparatus (20) to the observed object) causes a rotation of the image display apparatus in the same direction of rotation (in relation to the direction from an observer to the image display apparatus).

The predetermined angle range may comprise 360 degrees, i.e., a full circle. In particular, the controller is embodied in such a way that the second angle corresponds to the first angle or to a predetermined fraction of the first angle at all times. Further, the controller can be embodied in such a way that limits or boundary conditions on the part of the image display apparatus, for example a restricted length or elasticity of a cable for transmitting an image signal or electric power, or a restricted angle range of a joint of the holding apparatus are taken into account.

In a system as described here, the controller is embodied, in particular, to control the drive device in such a way that, within a predetermined angle range, any or each rotation of a camera, which is coupled to the image capturing apparatus, relative to the image capturing apparatus through a first angle about the viewing direction of the camera causes a rotation of the image display apparatus through a second angle, wherein the second angle equals the first angle or the second angle is a predetermined fraction of the first angle or a predetermined function of the first angle or a predetermined function of the angle position of the image capturing apparatus.

By way of example, many endoscopes do not comprise a camera themselves but only comprise an eyepiece, a camera being able to be optically and mechanically coupled thereto. A rotation of the camera relative to the endoscope (or relative to any other image capturing apparatus) in a direction of rotation causes a rotation of the image represented by the image signal of the camera in the opposite direction of rotation. This rotation can be compensated by an appropriate rotation of the image display apparatus. Alternatively, the rotation of the camera relative to the image capturing apparatus can be implemented by a processing of the image signal produced by the camera, wherein the image represented by the image signal is rotated.

In principle, the function that sets the orientation of the image display apparatus in space in a system as described here may additionally also still take account of other factors. By way of example this could include the position and/or orientation of the user relative to the operating field and/or relative to the image display apparatus. To this end, means suitable for capturing the position and orientation of a person, for example a marking that is fastened to the person and is captured by a camera, or means for identifying the eyes of the user and their viewing direction may be provided. This can prevent the image display apparatus from being poorly visible or no longer visible at all to a user, and a position of the image display apparatus relative to the user can be optimized.

In a system as described here, the holding apparatus comprises, in particular, one or more hinges that allow a rotation of the image display apparatus about a central surface normal of an image display surface of the image display apparatus, with the drive device comprising one or more motors or actuators for rotating the image display apparatus about the central surface normal of the image display surface of the image display apparatus.

The holding apparatus may comprise a single joint in the form of a rotational bearing that facilitates a rotation of the image display apparatus about the central surface normal of the image display surface of an image display apparatus mechanically connected to the holding apparatus as intended.

In this case, the drive device, too, only comprises one motor or one actuator, in particular, for rotating the image display apparatus mechanically connected to the holding apparatus as intended. Alternatively, the holding apparatus can be embodied as a hexapod, for example, or can comprise one or more hexapods. In this case, a rotation of the image display apparatus is implemented, in particular, by shortening a plurality of arms and/or simultaneously lengthening other arms, each by way of a motor or actuator.

A system as described here further comprises, in particular, an image signal processing apparatus comprising an image signal input for receiving a first image signal from the image capturing apparatus and an image signal output for providing a second image signal to the image display apparatus, wherein the image signal processing apparatus is embodied to rotate the image displayed by the image display apparatus when the image capturing apparatus is rotated.

To this end, the image signal processing apparatus comprises, in particular, a signal input for receiving a signal that represents an orientation or a change in the orientation of the image capturing apparatus in space or that facilitates a determination of the orientation or the change in the orientation of the image capturing apparatus. Alternatively, the image signal processing apparatus can be embodied to identify a rotation of the image capturing apparatus by analyzing the image captured by the image capturing apparatus, i.e., the image signal produced by the image capturing apparatus or the camera thereof, and cause a corresponding rotation of the image represented by the image signal supplied to the image display apparatus.

The image signal processing apparatus can be integrated with the controller and/or with other components of the system.

A controller for a system as described here comprises, in particular, a signal input for receiving a signal that represents an orientation or a change in the orientation of the viewing direction of the image capturing apparatus in space or that facilitates a determination of the orientation or the change in the orientation of the viewing direction of the image capturing apparatus, and a control signal output, which is couplable to the control signal input of the controllable drive device, for providing a control signal for controlling the controllable drive device, wherein the controller is embodied and provided to control the controllable drive device in such a way that, within a predetermined range of possible orientations of the viewing direction of the image capturing apparatus in space, the orientation of the image capturing apparatus in space is a predetermined function of the orientation of the viewing direction of the image capturing apparatus in space.

The controller may comprise further features of the controller of a system described herein.

A method for displaying an image captured by means of a movable image capturing apparatus (20) comprises a step of capturing the orientation of the viewing direction of the image capturing apparatus (20) in space by means of a sensor and a step of setting the orientation of the image display apparatus in space depending on the orientation of the image capturing apparatus (20) in space.

The method is able to be carried out, in particular, using a system as described herein. A system as described herein is embodied, in particular, for a method as described herein. A controller as described herein is embodied, in particular, to control a method as described herein.

When capturing the orientation of the image capturing apparatus in space, in particular the direction of the gravitational force and/or a linear acceleration and/or a rotation (for example, by means of a gyroscope, a vibrating structure gyroscope or any other rate sensor) and/or a direction and/or a strength of a magnetic field are captured. In particular, the sensor is part of a image capturing apparatus or mechanically rigidly connected thereto (releasable in nondestructive fashion or not releasable in nondestructive fashion). A signal produced by the sensor can be transferred electrically, optically or by means of an electromagnetic wave to a controller for the purposes of controlling the method.

As an alternative or in addition thereto, one or more images of an operating field can be captured in order to identify the image capturing apparatus in the image or in the images and in order to determine the orientation and the position of the image capturing apparatus therefrom. As an alternative or in addition thereto, electromagnetic waves that are produced or specularly reflected or diffusely reflected by the image capturing apparatus can be captured by means of one or more antennas or other receivers. The orientation of the image capturing apparatus can be deduced from the intensity or amplitude or power density and/or from the polarization and/or from the phase difference of a plurality of waves.

Further, in a method as described here, the orientation of the image capturing apparatus in space, in particular, is presented graphically or numerically on an image display surface of the image display apparatus.

The orientation of the image capturing apparatus in space can be represented, for example, by a perspective illustration of an arrow that indicates a basic direction or by a reduced perspective illustration of a human body in the position of the patient. As an alternative or in addition thereto, angles can be output in analog fashion on scales or in digital fashion in the form of numbers.

A method as described here further comprises, in particular, a rotation of the image presented on the image display surface depending on a rotation of the image capturing apparatus about the viewing direction of the image capturing apparatus.

Thus, a rotation of the image capturing apparatus about the viewing direction of the image capturing apparatus may cause, alternatively or simultaneously, a rotation of the image presented on the image display surface of the image display apparatus relative to the image display apparatus and a rotation of the image display apparatus.

In a method as described here, the image presented on the image display surface is deformed depending on an orientation in the viewing direction of the image capturing apparatus in space.

In particular, the deformation is implemented in such a way that a perspective impression of an image that is pivoted or inclined in relation to the actual image display surface arises. By way of example, a greater pivot or inclination angle can also be presented without causing an inexpedient observation direction onto the image display surface of the image display apparatus by virtue of pivoting or inclining of the image capturing apparatus only partly causing a corresponding pivoting or inclining of the image display apparatus but additionally causing a corresponding deformation of the presented image.

BRIEF DESCRIPTION OF THE DRAWINGS

Embodiments are explained in more detail below on the basis of the attached figures. In detail.

DETAILED DESCRIPTION

Figure 1:
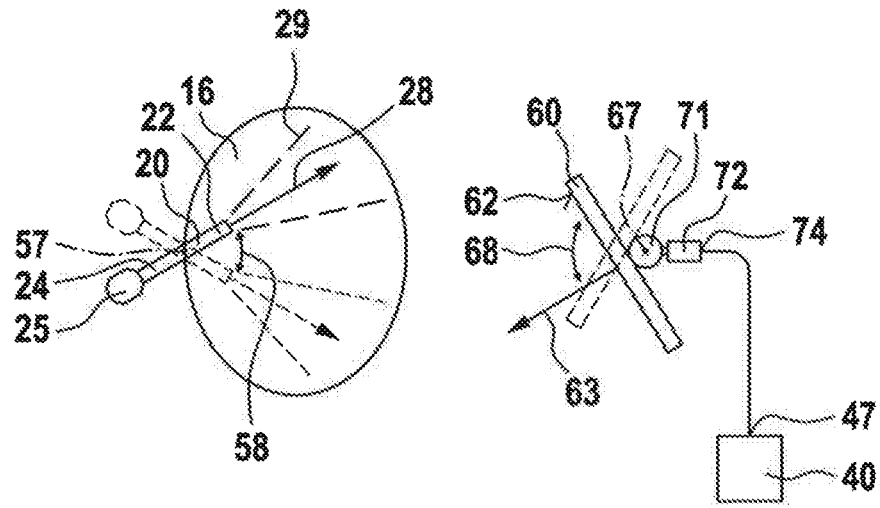
FIG. 1 shows a schematic illustration of a system for holding an image display apparatus.

FIG. 1 shows a schematic illustration of a cavity 16, indicated by its contour, in the body of a patient. A distal end 22 of an image capturing apparatus, specifically an endoscope 20, has been introduced into the cavity 16. A camera 25 is coupled to the proximal end 24 of the endoscope 20 or integrated into the proximal end 24 of the endoscope 20. Alternatively, the endoscope 20 may have a camera or one or more image sensors at its distal end 22 or at any other location.

The viewing direction 28 of the endoscope 20 is the direction from a light entry surface on the distal end 22 of the endoscope 20 to an article at a great distance, which appears in the center of an image captured by the endoscope 20. The edge of the region captured by the endoscope 20 is indicated by two lines 29 in FIG. 1. In the presented example, the viewing direction 28 of the endoscope 20 is parallel to the longitudinal axis of a straight shaft of the endoscope 20.

The endoscope 20 can—inter alia—be rotated or pivoted about a pivot axis or axis of rotation 57, which is orthogonal to the plane of the drawing of FIG. 1. By way of example, the pivot axis or axis of rotation 57 lies within a trocar tube, through which the endoscope is introduced into the cavity 16.

In FIG. 1, the endoscope 20 is presented in two orientations, specifically in a first orientation using solid lines and in a second orientation using dashed lines. The endoscope 20 can be pivoted back and forth between the two orientations (and further orientations). A double-headed arrow 58 indicates a pivot movement about the pivot axis or axis of rotation 57.

The endoscope 20 may have further degrees of freedom, more particularly a rotation about its viewing direction 28 and a rotation or pivoting about a further axis of rotation or pivot axis, which may be orthogonal to the pivot axis 57 and orthogonal to the viewing direction 28 of the endoscope 20. However, only the degree of freedom of the pivot movement 58 about the pivot axis or axis of rotation 57 is initially considered below.

An image captured by means of the endoscope 20 (in particular by the camera 25 or one or more image sensors of the endoscope 20) is transferred to a screen 60 as an image display apparatus by means of apparatuses not presented in FIG. 1, more particularly electrical or optical signal lines and, optionally, an image signal processing device. The image is displayed on an image display surface 62. In the presented example, the image display surface 62 is plane and the surface normal 63 of the image display surface 62 is parallel to the plane of the drawing of FIG. 1.

The screen 60 is held on a joint 71 which defines a pivot axis or axis of rotation 67. Thus, the screen 60 is able to be pivoted about the pivot axis 67. The pivot axis 67 is orthogonal to the plane of the drawing of FIG. 1 and parallel to the image display surface 62 of the screen 60.

The joint 71 is part of a movable holding apparatus, otherwise not presented in FIG. 1, for the alterable hold of the screen 60. This movable holding apparatus may have further degrees of freedom; however, initially, only the degree of freedom of pivoting or rotating 68 the screen about the axis of rotation or pivot axis 67, defined by the joint 71 and the pivot axis or axis of rotation 67, is discussed below.

A drive device 72 for moving the screen 60, specifically for pivoting the screen 60 about the pivot axis 67, is provided at the joint 71. A control signal input 74 of the drive device 72 is connected to a signal output 47 of the controller 40.

From a device not presented in FIG. 1, the controller 40 receives a signal that represents an orientation or a change in the orientation of the endoscope 20, more particularly the current viewing direction 28 and/or a change in the viewing direction 28, or that facilitates a determination of the orientation or the change in the orientation of the endoscope 20. When the controller receives a signal that represents a change in the orientation of the endoscope 20, the controller 40 determines the current orientation of the endoscope 20 by integrating the signal. When the controller 40 receives a signal that facilitates a determination of the orientation of the endoscope 20, the controller 40 determines the orientation of the endoscope 20 from the received signal. When the controller 40 receives a signal that facilitates the determination of a change in the orientation of the endoscope 20, the controller 40 determines the change in the orientation of the endoscope 20 and integrates said change in order to determine the current orientation of the endoscope 20. By way of example, the change in the orientation of the endoscope 20 can be specified in degrees per second for one degree of freedom.

Further, the controller 40 knows the current orientation of the screen 60, in particular, and compares the orientation of the screen 60 to the orientation represented by the received signal or the orientation of the endoscope 20 determined by the controller 40. The controller 40 produces a control signal for the drive device 72 in order at any time to move the screen 60 into an orientation that corresponds to, or is associated with, the current orientation of the endoscope 20.

In FIG. 1, the screen 60 is presented in two orientations, specifically in a first orientation using solid lines, which corresponds to the orientation of the endoscope 20 that is likewise presented using solid lines in FIG. 1, and a second orientation using dashed lines, which corresponds to the orientation of the endoscope 20 that is likewise presented using dashed lines in FIG. 1.

In the example shown in FIG. 1, the orientation of the screen 60 corresponds to the orientation of the endoscope 20 when the surface normal 63 of the image display surface 62 of the screen 60 is antiparallel to the viewing direction 28 of the endoscope 20. Alternatively, the controller 40 can control the drive device 72 in such a way, for example, that a predetermined difference angle lies between the surface normal 63 of the image display surface 62 of the screen 60 and the viewing direction 28 of the endoscope 20 at all times. Alternatively, the controller 40 can control the drive device 72 in such a way, for example, that an orientation of the screen 60 present at an initialization of the controller 40 or at any other defined time is associated with an orientation of the viewing direction 28 of the endoscope 20 present at the same time. In this case, the controller 40 can control the drive device 72 in such a way that every subsequent change in the orientation of the viewing direction 28 of the endoscope 20 through a certain angle causes a change in the orientation of the screen 60 by the same angle or by a predetermined fraction of the angle or by an angle that depends on the deviation of the orientation of the screen 60 from a predetermined basic orientation.

In the example presented in FIG. 1, the pivot axis 57, about which the endoscope 20 is able to be pivoted, and the pivot axis 67, about which the screen 60 is able to be pivoted, are parallel to one another and orthogonal to the plane of the drawing of FIG. 1. Both pivot axes 57, 67 can be, e.g., vertical, i.e., parallel to the direction of the gravitational force, or horizontal, i.e., orthogonal to the vertical, or point in any other directions. Deviating from the illustration in FIG. 1, the pivot axes 57, 67 may be non-parallel.

The holding apparatus presented in representative fashion by the joint 71, the controllable drive device 72 and the controller 40 form a system for holding the screen 60. The screen 60 is not a constituent part of this system but connected or connectable in mechanically rigid and nondestructively releasable fashion with the holding apparatus represented by the joint 71. Alternatively, the screen 60 may be part of the system. The endoscope 20, too, is not part of the system although it may be part of said system.

Figure 2:
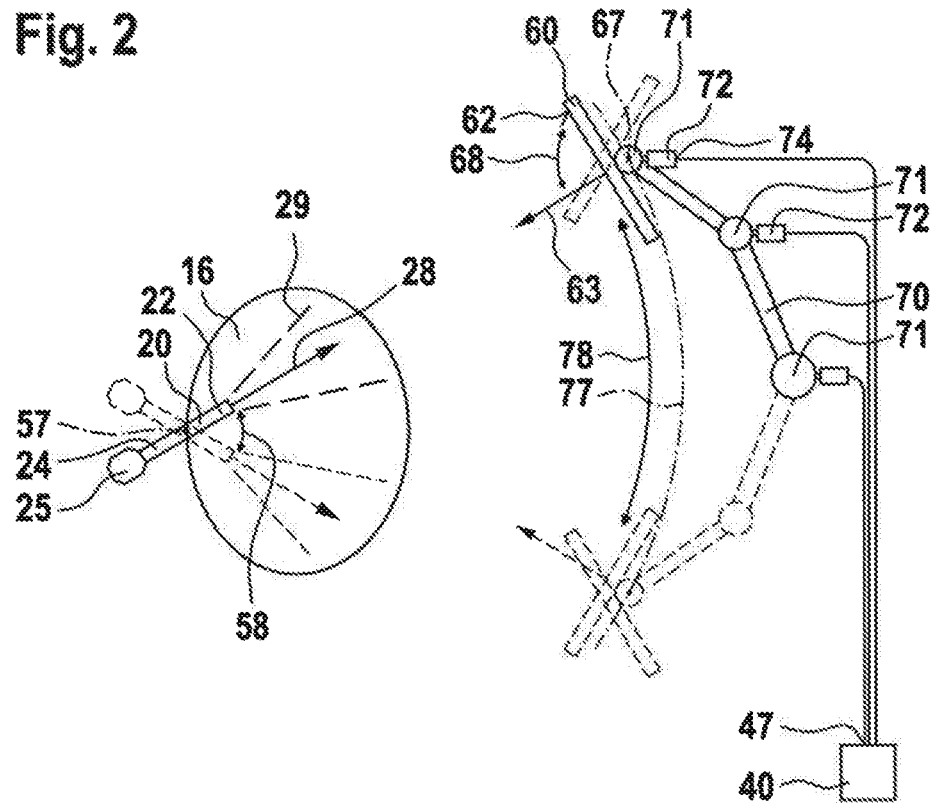
FIG. 2 shows a schematic illustration of a further system for holding an image display apparatus.

FIG. 2 shows a schematic illustration of an endoscope 20, the distal end 22 of which is disposed in a cavity 16 in the body of a patient, of a screen 60 and of a system made of a movable holding apparatus 70, a multi-part controllable drive device 72 and a controller 40. In particular, the endoscope 20 and the screen 60 correspond to the endoscope 20 and the screen 60 of the embodiment presented on the basis of FIG. 1. The controller 40 and the movable holding apparatus 70 with the multi-part controllable drive device 72 are similar in some features, properties and functions to the controller 40 and the holding apparatus represented by the joint 71, which are presented on the basis of FIG. 1. In particular, features, properties and functions of the controller 40, of the holding apparatus 70 and of the multi-part drive device 72 by which these differ from the example presented on the basis of FIG. 1 are described below.

The holding apparatus 70 shown in FIG. 2 comprises a plurality of joints 71 that define a plurality of pivot axes. These pivot axes may be orthogonal to the plane of the drawing of FIG. 2 and/or may point in one or more other directions. In the presented example, the joint 71 closest to the screen 60 defines a pivot axis 67 that is orthogonal to the plane of the drawing of FIG. 2. A part of the multi-part drive device 72 is associated with each joint 71. Each part of the drive device 72 is coupled to a signal output 47 of the controller 40.

The controller 40 is embodied to control the multi-part drive device 72 in such a way that every pivoting movement of the endoscope 20 about the pivot axis 57 causes an associated pivot movement of the screen 60 about the pivot axis 67 and, at the same time, a translational movement 78 of the screen along a curved, more particularly arcuate path 77. In particular, the controller 40 is embodied to control the multi-part drive device 72 in such a way that the surface normal 63 of the image display surface 62 of the screen 60 and the curved path 77 lie in a plane at each orientation and position of the screen 60. Two orientations and positions of the screen 60 are indicated in FIG. 2, specifically an orientation and a position of the screen 60 using solid lines, which are associated with the orientation of the endoscope 20 likewise presented using solid lines in FIG. 2, and an orientation and a position of the screen 60 using dashed lines, which are associated with the orientation of the endoscope 20 indicated using dashed lines in FIG. 2.

In the examples presented on the basis of FIGS. 1 and 2, only one rotational degree of freedom of the pivot movement 58 of the endoscope 20 about the pivot axis or axis of rotation 57 and one rotational degree of freedom of the pivot movement 68 of the screen 60 about the pivot axis or axis of rotation 67 are described in each case. In the example presented on the basis of FIG. 2, this is complemented by a translational degree of freedom of the movement 78 of the screen 60 along the path 77, with the controller 40 linking the rotational degree of freedom and the translational degree of freedom of the screen 60 with one another in such a way that a certain position of the screen 60 is associated with each orientation of the screen 60.

In addition to the degrees of freedom presented on the basis of FIGS. 1 and 2, the controller may capture one or more further rotational degrees of freedom of the endoscope 20 and of the camera 25, specifically a pivot movement of the endoscope 20 about a further pivot axis that, in particular, is orthogonal to the pivot axis 57 presented in FIGS. 1 and 2 and/or a rotation of the endoscope 20 about the viewing direction 28 and/or a rotation of the camera 25 relative to the endoscope 20, for example about the optical axis of an eyepiece at the proximal end 24 of the endoscope 20 and of an objective lens of the camera 25.

In this case, the controller can be embodied to additionally pivot or rotate the screen 60 about one or more further pivot axes or axes of rotation depending on the movements of the endoscope 20. The holding apparatus 70, the multi-part drive device 72 and the controller 40 can be embodied in such a way that the screen 60, depending on the viewing direction 28 of the endoscope 20, is pivoted about two pivot axes or axes of rotation that are orthogonal to one another and not parallel to the surface normal 63 of the image display surface 62 of the screen 60 and optionally moved along a curved surface at the same time. Here, every orientation of the viewing direction 28 of the endoscope 20 is associated with an orientation and a position of the screen 60.

As an alternative or in addition thereto, the holding apparatus 70 may comprise a joint that defines an axis of rotation parallel to the surface normal 63 of the image display surface 62 of the screen 60 and the controller 40 may be embodied in such a way that a rotation of the endoscope 20 about its viewing direction 28 and/or a rotation of the camera 25 relative to the endoscope 20 causes a rotation of the screen 60 about the surface normal 63 of the image display surface 62.

Figure 3:
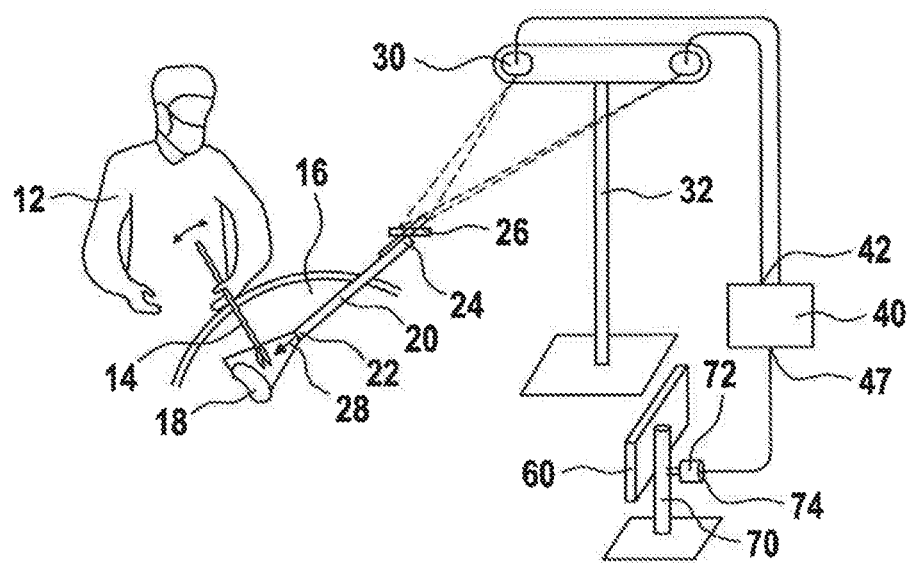
FIG. 3 shows a schematic illustration of a further system for holding an image display apparatus.

FIG. 3 shows a schematic illustration of a physician 12 with a medical instrument 14, for example a pair of scissors or forceps. The distal end of the medical instrument 14 is disposed in a cavity 16 in the body of a patient in order to facilitate a medical measure on an organ or any other object in the body of the patient. The distal end 22 of an endoscope 20 is likewise disposed in the cavity 16 in the body of the patient. The viewing direction 28 of the endoscope 20 is directed to the distal end of the instrument 14 and to the organ 18.

An image of the distal end of the medical instrument 14 and of the organ 18 in the cavity 16 in the body of the patient is captured by means of the endoscope 20. To this end, one or more image sensors of the endoscope 20 produce an image signal that represents the captured image. Alternatively, in a manner similar to the examples presented on the basis of FIGS. 1 and 2, a camera is arranged at the proximal end 24 of the endoscope 20, said camera, for example, being coupled to an eyepiece of the endoscope 20, capturing an image produced by the endoscope 20 and producing an image signal representing the image.

The screen 60 is arranged opposite the medical member of staff 12 in such a way that the medical member of staff 12 is able to observe the image display surface of the screen 60 with a posture that is as little tiring as possible. The screen 60 receives the image signal produced by means of the endoscope (i.e., by the endoscope itself or by a camera optically coupled to the endoscope) and displays the image represented by the image signal.

The screen 60 is held by a movable holding apparatus 70 that—similar to what is presented on the basis of FIGS. 1 and 2—comprises one or more joints, which are not presented in FIG. 3. A single-part or multi-part drive device 72 for moving the holding apparatus and the screen 60 is coupled to a signal output 47 of a controller 40. Signal inputs 42 of the controller 40 are held with two or more cameras 30 on a stand 32. A structure 26 is arranged at the proximal end 24 of the endoscope 20. The structure 26 is cruciform in the presented example. The structure 26 renders an optical identification of the proximal end 24 of the endoscope 20 and its position and orientation simpler and/or more reliable.

The cameras 30 are directed on the operating field and capture the proximal end 24 of the endoscope 20 with the structure 26. The controller 40 receives image signals from the cameras 30 and evaluates the latter in order to identify the structure 26 therein and in order to determine the position and the orientation of the proximal end 24 of the endoscope 20. Depending on the position and orientation of the proximal end 24 of the endoscope 20 as determined by the controller 40 by means of the cameras 30, the controller 40 controls—by way of a control signal at the control signal input 74 of the drive device 72—the drive device 72 in such a way that the screen 60 always has an orientation that corresponds to, or is associated with, the simultaneously present orientation of the endoscope 20, more particularly of the viewing direction 28 of the endoscope 20.

The controller 40, the holding apparatus 70 and the drive device 72 form a system for holding the screen 60.

Figure 4:
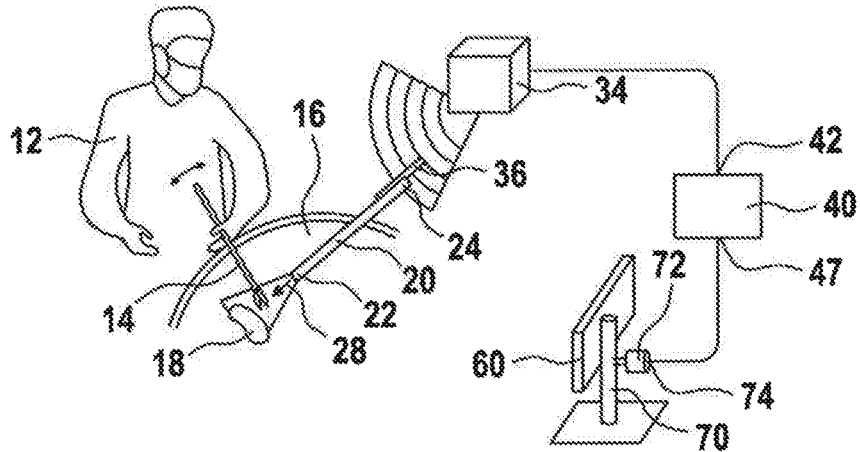
FIG. 4 shows a schematic illustration of a further system for holding an image display apparatus.

FIG. 4 shows a schematic illustration of a physician 12 with a medical instrument 14, the distal end of which is disposed in a cavity 16 in the body of a patient. The distal end 22 of an endoscope 20 is likewise disposed in the cavity 16. The viewing direction 28 of the endoscope 20 is directed on an organ 18 and the distal end of the medical instrument 14. Opposite the medical member of staff 12, a screen 60 is arranged on a movable holding apparatus 70, said screen displaying an image captured by means of the endoscope 20. A signal output 47 of a controller 40 is coupled to a control signal input 74 of a drive device 72 on the movable holding apparatus 70 such that the controller 40 can control the drive device 72.

The endoscope 20, the controller 40, the screen 60, the movable holding apparatus 70 and the drive device 72 are similar in some features, properties and functions to the endoscope 20, the controller 40, the screen 60, the movable holding apparatus 70 and the drive device 72, which are presented on the basis of FIG. 3. In particular, the controller 40, the holding apparatus 70 and the drive device 72 form a system for holding the screen 60. In particular, features, properties and functions in which the endoscope 20 and the controller 40 differ from the example presented on the basis of FIG. 3 are described below.

At its proximal end 24, the endoscope 20 comprises a transponder 36 for receiving an electromagnetic wave and for transmitting an electromagnetic wave that has been modified depending on the orientation of the endoscope 20 and of the transponder 36. A signal input 42 of the controller 40 is coupled to a device 34 for transmitting an electromagnetic signal and for receiving an electromagnetic signal emanating from the transponder 36.

The transponder 36 at the endoscope 20 can be embodied so as to capture the orientation of the endoscope 20 itself and encode information about the orientation of the endoscope 20 in an electromagnetic signal sent back to the device 34. Alternatively, the transponder 36 can be embodied as a purely passive component, wherein the device 34 and/or the controller 40 derive or determine the orientation of the transponder 36 and of the endoscope 20, for example from a polarization direction, a power density or a phase angle of an electromagnetic signal transmitted from the transponder 36 to the device 34. Both the device 34 and the transponder 36 may each comprise one or more antennas for different polarizations and/or emission characteristics and/or for electromagnetic waves with different phase angles.

During a medical measure, the device 34 produces an electromagnetic wave that is specularly reflected or diffusely reflected by the transponder 36 on the endoscope 20. The device 34 receives the electromagnetic wave specularly reflected or diffusely reflected by the transponder 36. Here, the device 34 receives, in particular, the information encoded in the sent-back electromagnetic wave and/or the intensity or amplitude or power density of the received electromagnetic wave and/or the polarization of the electromagnetic wave and/or the phase angle of the electromagnetic wave. If the transponder 36 comprises a plurality of antennas or comprises a plurality of partial transponders, the device 34 can capture the amplitudes, polarizations and/or phase angles of the electromagnetic waves emanating from these antennas or partial transponders in absolute terms or at least relative to one another.

The device 34 can be embodied to determine the orientation of the transponder 36 and of the endoscope 20 from the received electromagnetic waves and to transmit this information to the controller 40. Alternatively, the device 34 can be embodied to transmit raw data to the controller 40, with the orientation of the transponder 36 and of the endoscope 20 only being determined from the raw data by the controller 40.

As an alternative to a transponder 36, the endoscope 20 can be provided with one transmitter or a plurality of transmitters that transmit one or more electromagnetic waves by way of one or more antennas. Here, the device 34 receives, in particular, the information encoded in the electromagnetic waves transmitted by the transmitter or transmitters and/or the intensity or amplitude or power density of the received electromagnetic wave and/or the polarization of the electromagnetic wave and/or the phase angle of the electromagnetic wave. If the transmitter comprises a plurality of antennas or if a plurality of transmitters are provided, the device 34 can capture the amplitudes, polarizations and/or phase angles of the electromagnetic waves emanating from these antennas or transmitters in absolute terms or relative to one another.

Similar to what was presented on the basis of FIGS. 1 to 3, the controller 40 controls the drive device 72 in such a way that the orientation of the screen 60 always corresponds to an intended orientation of the screen 60, which is associated with the simultaneously present orientation of the endoscope 20.

Figure 5:
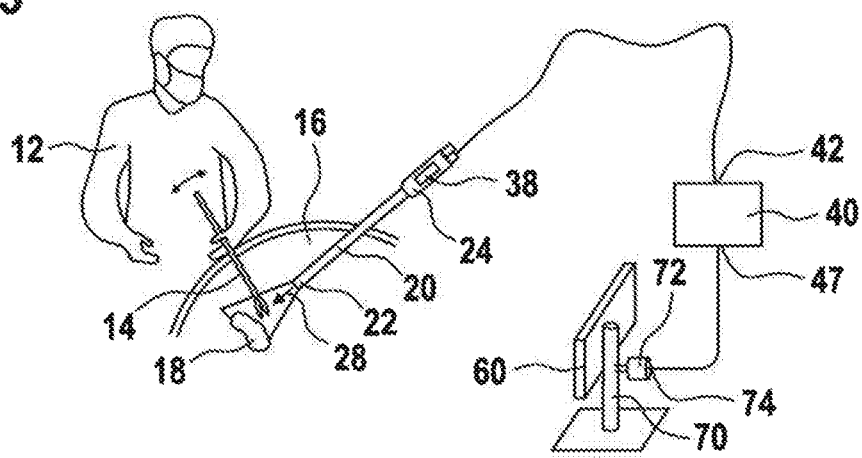
FIG. 5 shows a schematic illustration of a further system for holding an image display apparatus.

FIG. 5 shows a schematic illustration of a physician 12 with a medical instrument 14. The distal end of the medical instrument 14 and the distal end 22 of an endoscope 20 are disposed in a cavity 16 in the body of a patient for the purposes of a medical measure. The viewing direction 28 of the endoscope 20 is directed to the distal end of the instrument 14 and an organ 18 in the cavity 16. The proximal end 24 of the endoscope 20 is arranged outside of the cavity 16.

The endoscope 20, the controller 40, the screen 60, the movable holding apparatus 70 and the drive device 72 are similar in some features, properties and functions to the endoscopes 20, the controllers 40, the screens 60, the movable holding apparatuses 70 and the drive devices 72, which are presented on the basis of FIGS. 3 and 4. In particular, the controller 40, the holding apparatus 70 and the drive device 72 form a system for holding the screen 60. In particular, features, properties and functions in which the endoscope 20 and the controller 40 differ from that presented on the basis of FIG. 3 are described below.

In or at its proximal end 24, the endoscope 20 comprises a sensor 38. The sensor 38 is embodied and provided to capture the direction of the gravitational force and/or to capture a linear or translational acceleration and/or to capture a rotation rate and/or to capture the direction and/or the strength of the magnetic field or any other directed field. The sensor 38 is coupled to a signal input 42 of the controller 40. From the sensor 38, the controller 40 receives the captured information and determines the orientation of the sensor 38 and of the endoscope 20 in space therefrom. As an alternative thereto, the sensor 38 or a device disposed downstream of the sensor in or at the endoscope 20 determines the orientation of the sensor 38 and of the endoscope 20 in space and transmits this information to the controller 40.

In a manner similar to what was presented on the basis of FIGS. 1 to 4, the controller 40 controls the drive device 72 in such a way that the orientation of the screen 60 always corresponds to an intended orientation of the screen 60, which is associated with the simultaneously present orientation of the endoscope 20.

Figure 6:
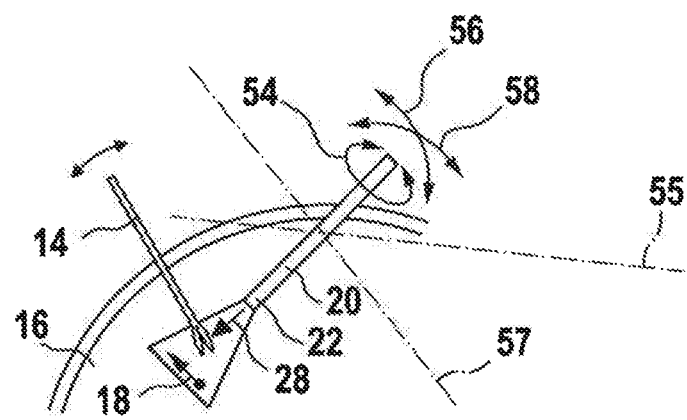
FIG. 6 shows a schematic illustration of an image capturing apparatus.

FIG. 6 shows a schematic illustration of an endoscope 20, the distal end 22 of which is disposed within a cavity 16 in the body of a patient and the proximal end 24 of which is disposed outside of said cavity. Further, a medical instrument 14, the distal end of which is disposed in the cavity 16, and an organ 18 in the cavity 16 are presented. The organ is represented by an arrow.

In FIG. 6, axes of rotation and associated movements in relation to the three rotational degrees of freedom are presented. A first rotational degree of freedom is formed by the rotation 54 about the viewing direction 28 of the endoscope 20. Further, the endoscope 20 can be rotated or pivoted about two axes of rotation or pivot axes 55, 57 that are orthogonal to one another and to the viewing direction 28 of the endoscope 20, corresponding to two further degrees of freedom. The pivot axes 55 is horizontal and orthogonal to the viewing direction 28; the pivot axis 57 is orthogonal to the viewing direction 28 and to the pivot axis 55. Alternatively, the pivot axis 57 can be vertical, i.e., parallel to the direction of the gravitational force. The pivot movement about the horizontal pivot axis 55 is indicated by a double-headed arrow 56; the pivot movement about the pivot axis 57 is indicated by a double-headed arrow 58.

Figure 7:
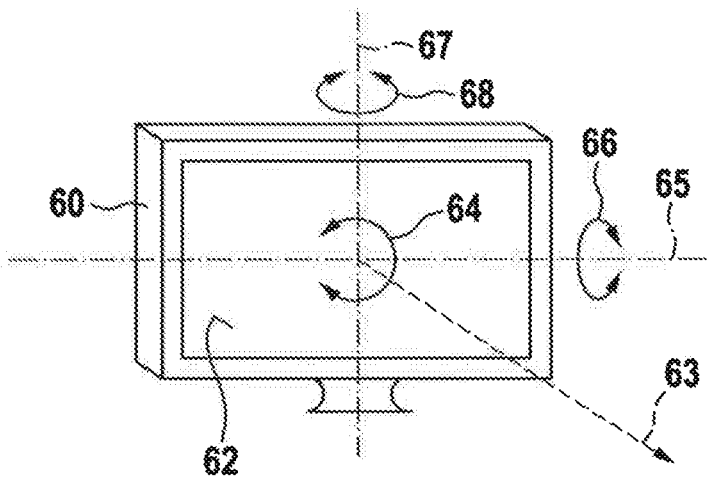
FIG. 7 shows a schematic illustration of an image capturing apparatus.

FIG. 7 shows a schematic illustration of a screen that can be a part of the systems presented on the basis of FIGS. 1 to 5 or that can be held by one of the systems presented on the basis of FIGS. 1 to 5.

The screen 60 has three rotational degrees of freedom. The rotation 64 about the surface normal 63 of the image display surface 62 of the screen 60 is referred to as first degree of freedom. Pivoting movements 66, 68 about two further pivot axes or axes of rotation 65, 67 correspond to two further degrees of freedom. In the presented example, the pivot axes 65, 67 are orthogonal to the surface normal 63 of the image display surface 62 of the screen 60 and to one another. Each pivot axis 65, 67 is parallel to two straight edge portions of the rectangular image display surface 62.

Figure 8:
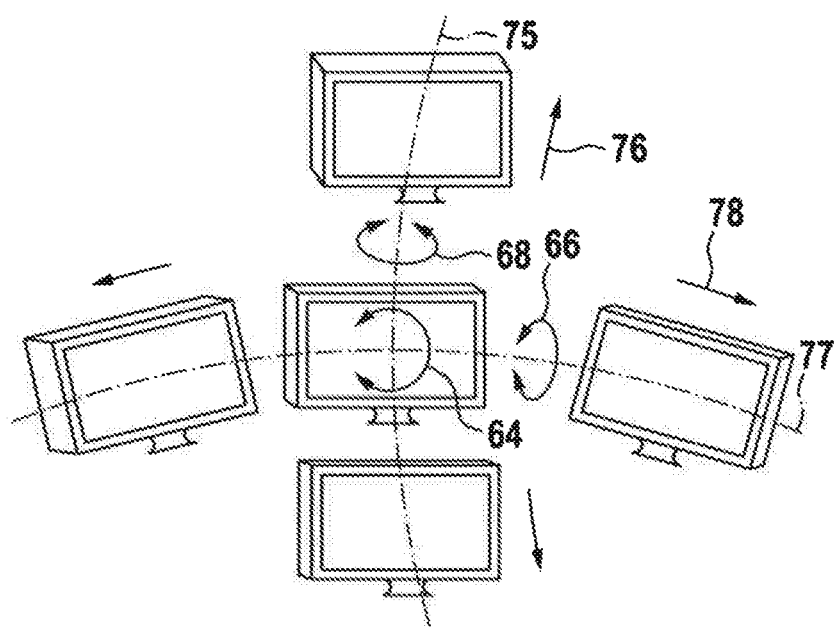
FIG. 8 shows a further schematic illustration of the image capturing apparatus of FIG. 7.

FIG. 8 shows a further schematic illustration of the screen of FIG. 7 with additional translational degrees of freedom. The screen 60 is able to be moved along a curved surface that is indicated by a path 75 lying in a vertical plane and a path 77 lying in a horizontal plane. Arrows 76 indicate movements of the screen 60 along the path 75 in a vertical plane; arrows 78 indicate movements of the screen 60 along the path 77 in a horizontal plane. The screen 60 is indicated in a main position using solid lines and in positions displaced along the paths 75, 77 using dashed lines. What is also indicated here is that—similar to what was presented on the basis of FIG. 2—a translational movement 76, 78 accompanies a pivoting movement 66, 68 of the screen 60.

The controller 40 of one of the systems presented on the basis of FIGS. 1 to 5 is embodied in such a way that, in particular, a rotation movement 54 of the endoscope 20 about its viewing direction 28 (cf., FIG. 6) causes a rotation movement 64 of the screen 60 about the surface normal 63 of the image display surface 62 (cf., FIG. 7). As an alternative or in addition thereto, the controller can be embodied to control the drive device in such a way that a pivot movement 56 of the endoscope 20 about a horizontal pivot axis 55 causes a pivot movement 66 of the screen 60 about a horizontal pivot axis 65 and, optionally, a simultaneous translation movement 76 along a path 75 in a vertical plane (cf., FIG. 8). As an alternative or in addition thereto, the controller 40 can be embodied to control the drive device in such a way that a pivot movement 58 of the endoscope 20 about a vertical or substantially vertical pivot axis 57 or about a pivot axis 57 that is orthogonal to the viewing direction 28 of the endoscope 20 and to a horizontal (cf., FIG. 6) causes a pivot movement 68 of the screen 60 about a vertical or substantially vertical axis 67 (cf., FIG. 7) and, optionally, an additional translational movement 78 along a horizontal path 77 (cf., FIG. 8).

Figure 9:
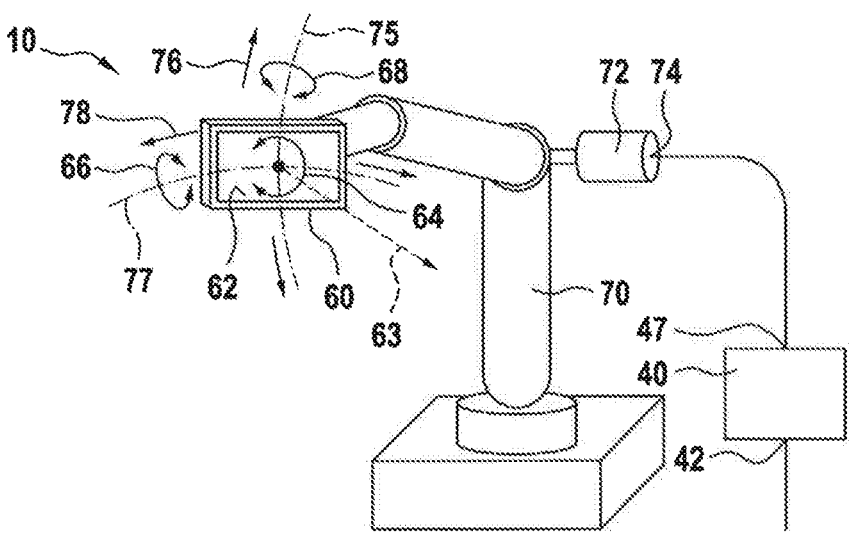
FIG. 9 shows a schematic illustration of a further system for holding an image display apparatus.

FIG. 9 shows a schematic illustration of a further system made of a controller 40 with a signal input 42 and a signal output 47, a movable holding apparatus 70 and a drive device 72. A control signal input 74 of the drive device 72 is coupled to the signal output 47 of the controller 40. The movable holding apparatus 70 in the example presented in FIG. 9 is presented in the style of an apparatus that is usually referred to as an industrial robot. The movable holding apparatus 70 comprises a plurality of joints, each with one or more rotational degrees of freedom, a plurality of parts of the drive device 72 being associated therewith. In FIG. 9, the drive device 72 is presented only at one joint 71 in a simplified fashion.

A screen 60 is held by the movable holding apparatus 70. Controlled by the controller 40 and driven by the drive device 72, the movable holding apparatus 70 can produce rotational and pivot movements 64, 66, 68 about three axes and translation movements 76, 78 in two orthogonal directions along a curved surface—indicated by two paths 75, 77.

Similar to what is presented on the basis of FIGS. 1 to 5, the controller 40 receives at its signal input 42 a signal that represents the current orientation of an endoscope (cf., FIG. 6) or any other image capturing apparatus or that allows the controller 40 to determine the current orientation of the endoscope or of the other image capturing apparatus. The controller 40 controls the drive device 72 in such a way that the orientation of the screen 60 in space (cf., FIG. 7) always corresponds to an intended orientation, which is associated with the currently present orientation of the endoscope or of the other image capturing apparatus. Optionally, the controller 40 controls the drive device 72 in such a way that the position of the screen (cf., FIG. 8), too, always corresponds to an intended position that is associated with the currently present orientation of the endoscope or of the other image capturing apparatus.

Figure 10:
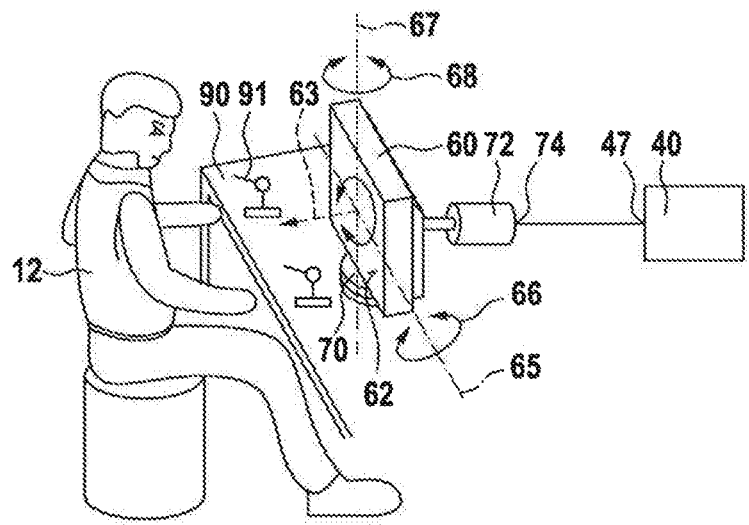
FIG. 10 shows a schematic illustration of a further system for holding an image display apparatus.

FIG. 10 shows a schematic illustration of a medical member of staff 12 at a console 91 of a da Vinci surgical system or a similar surgical system. Provided at the console 90 there are a plurality of input appliances 91, for example joysticks, by means of which the medical member of staff 12 can control the surgical system. An image capturing apparatus, for example a rigid or flexible endoscope, which can be inserted into the body of a patient and which is not presented in FIG. 10, is part of the surgical system. An image captured by the image capturing apparatus is displayed on the screen 60 or by any other image display apparatus. The orientation of the image capturing apparatus in space can be altered by rotating or pivoting about one or more axes of rotation or pivot axes. The orientation of the image capturing apparatus in space is known to the surgical system, in particular from the controller of same.

The screen 60 is held by a movable holding apparatus 70 that can be moved by a drive device 72. A signal input 74 of the drive device 72 is coupled to a signal output 47 of a controller 40. The controller 40, the movable holding apparatus 70 and the drive device 72 form a system with similar features, characteristics and functions as the systems described on the basis of FIGS. 1 to 5 and 9. The controller sets the orientation of the screen 60 depending on the orientation of the image capturing apparatus.

Figure 11:
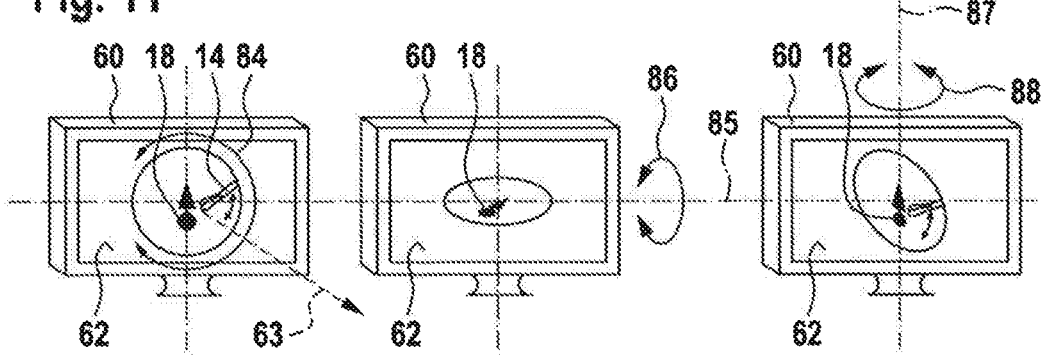
FIG. 11 shows schematic illustrations of an image display apparatus.

FIG. 11 shows schematic illustrations of a screen 60 that is similar to the screen of the systems presented on the basis of FIGS. 1 to 5, 9 and 10. In all three illustrations of the screen 60 in FIG. 11, an image is reproduced on the image display surface 62, as may be captured by the endoscope 20 in the situation presented in FIG. 6. Visible in each case are the distal end of the medical instrument 14 and the organ 18 with an arrow-shaped structure.

In FIG. 11, left, an arrow 84 represents a rotation of the image displayed on the screen 60, relative to the image display surface 62 about the surface normal 63 of the image display surface 62 as an axis of rotation. This arrow 84 of the displayed image relative to the image display surface 62 can complement or replace a rotation of the screen 60 about the surface normal 63 of the image display surface 62 of the screen 60 (cf., FIGS. 7 to 10).

FIG. 11, center, indicates a deformation of the image displayed on the image display surface 62, said deformation giving an observer the impression of a pivoting movement 86 of the displayed image about a horizontal pivot axis 85. This deformation of the displayed image, displayed in the center of FIG. 11, can complement or replace a pivot movement 66 of the screen 60 about a horizontal pivot axis 65 (cf., FIGS. 7 to 10).

FIG. 11, right, indicates a deformation of the image displayed on the image display surface 62, said deformation giving an observer the impression of a pivoting movement 88 of the displayed image about a vertical pivot axis 87. The deformation of the displayed image, displayed to the right of FIG. 11, can complement or replace a pivot movement 68 of the screen 60 about a vertical pivot axis 67 (cf., FIGS. 7 to 10).

By virtue of a rotation or pivot movement 54, 56, 58 (cf., FIG. 6) of an image capturing apparatus 20 only partly causing a corresponding rotation or pivot movement 64, 66, 68 of the screen 60 but, complementing this, a rotation 84 and/or a deformation of the displayed image that gives the impression of a pivot movement 86, 88, it is possible to avoid an inexpedient viewing angle for the medical member of staff 12 in relation to the screen 60 and/or facilitate a holding apparatus for the screen 60 that is simpler, more cost-effective, more compact and/or requires less installation space.

The rotation and/or deformation of the displayed image shown in FIG. 11 can be implemented by an image processing device that can be controlled by the controller 40 (cf., FIGS. 1 to 5, 9 and 10) and/or integrated in the latter.

Figure 12:
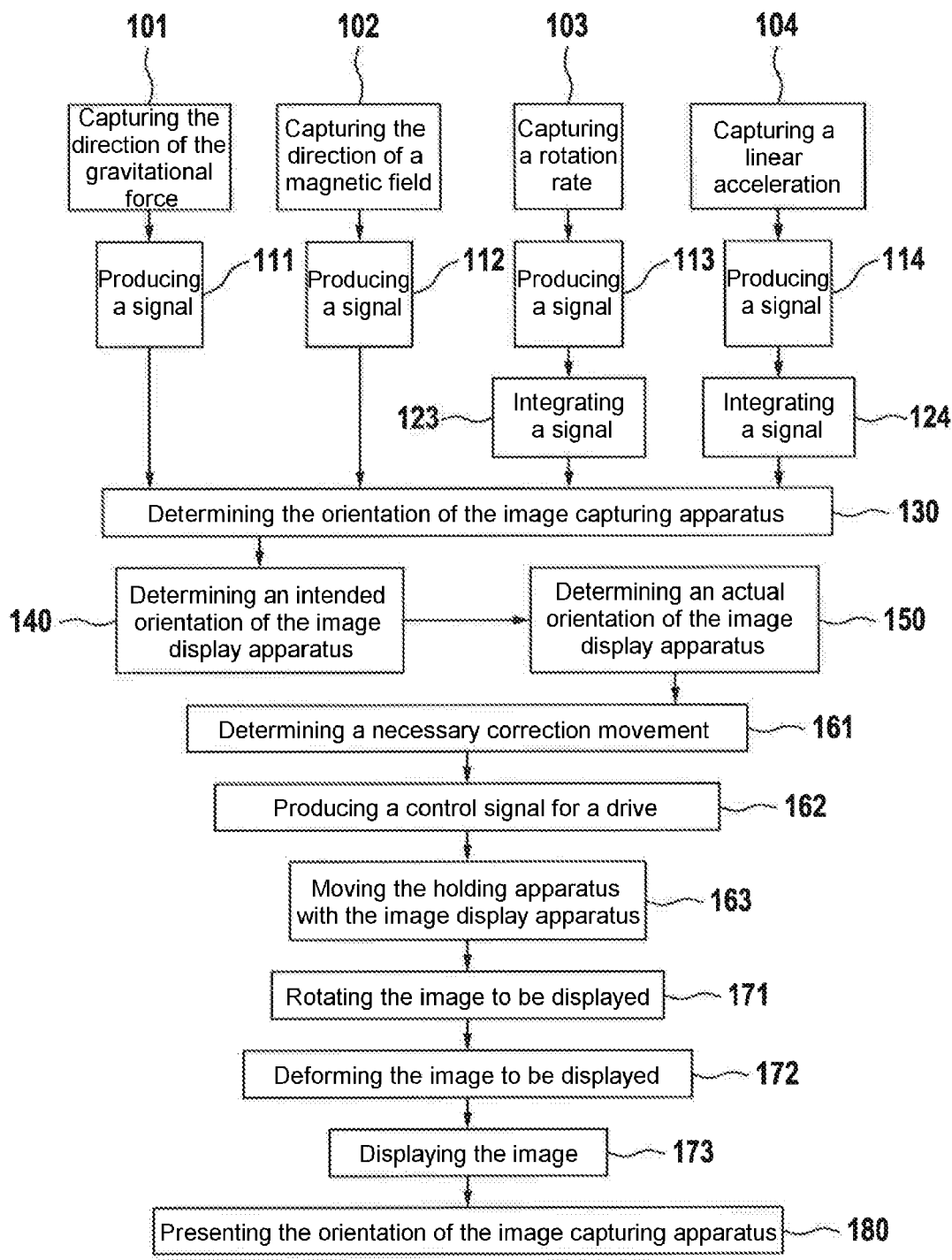
FIG. 12 shows a schematic flowchart of a method for displaying an image.

FIG. 12 shows a schematic flowchart of a method for displaying an image captured by means of a movable image capturing apparatus (20). In particular, the method is performable by means of any one of the systems presented on the basis of FIGS. 1 to 11. Therefore, the reference signs of FIGS. 1 to 11 are used below in exemplary fashion. However, the method is also performable by systems that differ in one or more features, properties and functions from the systems presented on the basis of FIGS. 1 to 11.

In a step 101, a sensor 38, which is arranged in or at an image capturing apparatus 20 and rigidly connected to the image capturing apparatus 20, captures a direction of the gravitational acceleration produced by the Earth. At the same time, or immediately thereafter, a signal that represents the direction of the gravitational force relative to the sensor is produced in a further step 111. Therefore, the orientation of the image capturing apparatus 20 relative to the vertical can be deduced from the produced signal.

In a further step 102, a sensor 38, which is arranged in or at an image capturing apparatus 20 and rigidly connected to the image capturing apparatus 20, captures the direction of the magnetic field relative to the sensor and hence relative to the image capturing apparatus 20. By way of example, the magnetic field is the Earth's magnetic field or an artificially produced magnetic field. A signal representing the direction of the magnetic field relative to the sensor 38 and hence relative to the image capturing apparatus 20 is produced in a further step 112, which occurs simultaneously or immediately thereafter. The orientation of the sensor 38 and hence the orientation of the image capturing apparatus 20 relative to magnetic field can be deduced from the signal.

In a further step 103, a sensor 38, which is arranged in or at the image capturing apparatus 20 and rigidly connected to the image capturing apparatus 20, captures a rotation rate of the sensor 38 and hence of the image capturing apparatus 20, too. This may comprise capturing the rotation rate and the direction of the current axis of rotation or capturing rotation rates in relation to a plurality of orthogonal reference axes. A signal representing the rotation rate captured in step 103 is produced in a step 113, which occurs simultaneously or immediately thereafter. In a subsequent step 123, the signal produced in step 113 is integrated over time. If the angle position of the sensor 38 and of the image capturing apparatus 20 is known at an initial time, the angle position or orientation of the sensor 38 and of the image capturing apparatus 20 present can be deduced at any later time from the integrated signal.

In a further step 104, a sensor 38, which is arranged in or at the image capturing apparatus 20 and rigidly connected to the image capturing apparatus 20, captures a linear or translational acceleration. Capturing the acceleration may comprise capturing the magnitude and the direction of the acceleration. Alternatively, capturing the acceleration may comprise capturing a plurality of components (for example, parallel to the axes of a local or global Cartesian coordinate system). A signal representing the captured acceleration is produced in a step 114, which occurs simultaneously or immediately thereafter. The produced signal is integrated in a subsequent step 124. If the position of the sensor 38 and of the image capturing apparatus 20 is known at an initial time, the position of the sensor 38 and of the image capturing apparatus 20 present at any later time can be calculated or determined at the later time from the integrated signal.

Steps 101 and 111, steps 102 and 112, steps 103, 113 and 123 and steps 104, 114, 124 represent alternatives that may be alternatively or simultaneously present in a method.

The orientation of the image capturing apparatus 20 is determined in a further step 130 on the basis of the signal or signals produced by the sensor 38 or the sensors in or at the image capturing apparatus 20.

An intended orientation of an image display apparatus 60 is determined from the orientation of the image capturing apparatus 20 in a further step 140. The intended orientation of the image display apparatus may be identical to the orientation of the image capturing apparatus or may be any desired function of the orientation of the image capturing apparatus.

An actual orientation of the image display apparatus 60 is determined in a further step 150; said actual orientation may be known, for example, from the performed number of steps of stepper motors or of position or angle sensors on joints of a holding apparatus, which holds the image display apparatus.

A necessary correction movement of the image display apparatus is determined in a further step 161 from the intended orientation and the actual orientation of the image display apparatus 60.

A control signal for a drive device 72 of the movable holding apparatus 70 for the image display apparatus 60 is produced in a further step 162 from the required correction movement.

Step 130, step 140, step 150, step 161 and step 162 are performed, in particular, by a controller 40, which may be part of the image capturing apparatus 20 or part of the drive device 72 for the movable holding apparatus or part of the image display apparatus 60 or an independent component.

The holding apparatus 70 holding the image display apparatus 60 is moved in accordance with the control signal in a further step 163.

The image to be displayed by the image display apparatus 60 is rotated in a further step 171. The image to be displayed by the image display apparatus 60 is deformed in a further step 172 in order to give an observer the impression of the displayed image being pivoted relative to the image display apparatus 60 about an axis 85, 87.

Step 163, step 171 and step 172 represent alternatives that, together or alternatively, may be part of the method shown in FIG. 12.

The image is displayed by the image display apparatus 60 in a step 173.

The orientation of the image capturing apparatus 20 in space is presented graphically or numerically on the image display apparatus 60 in a further and optional step 180. By way of example, this can be implemented by a perspective presentation of an arrow that indicates a predetermined reference direction. The reference direction depends on the medical measure and its location, for example cranial, caudal, ventral or dorsal. Alternatively, orienting the image capturing apparatus 20 in space can be implemented, for example, by a reduced and perspective presentation of the patient's body at the edge of the image display surface 62 of the image display apparatus 60. As an alternative or in addition thereto, orienting the image capturing apparatus 20 in space can be implemented by specifying angles on analog scales or in the form of numerical values.

The steps of the method presented on the basis of FIG. 12 are repeated, in particular cyclically, wherein some steps may be carried out simultaneously or in a different sequence to the one presented.

Figure 13:
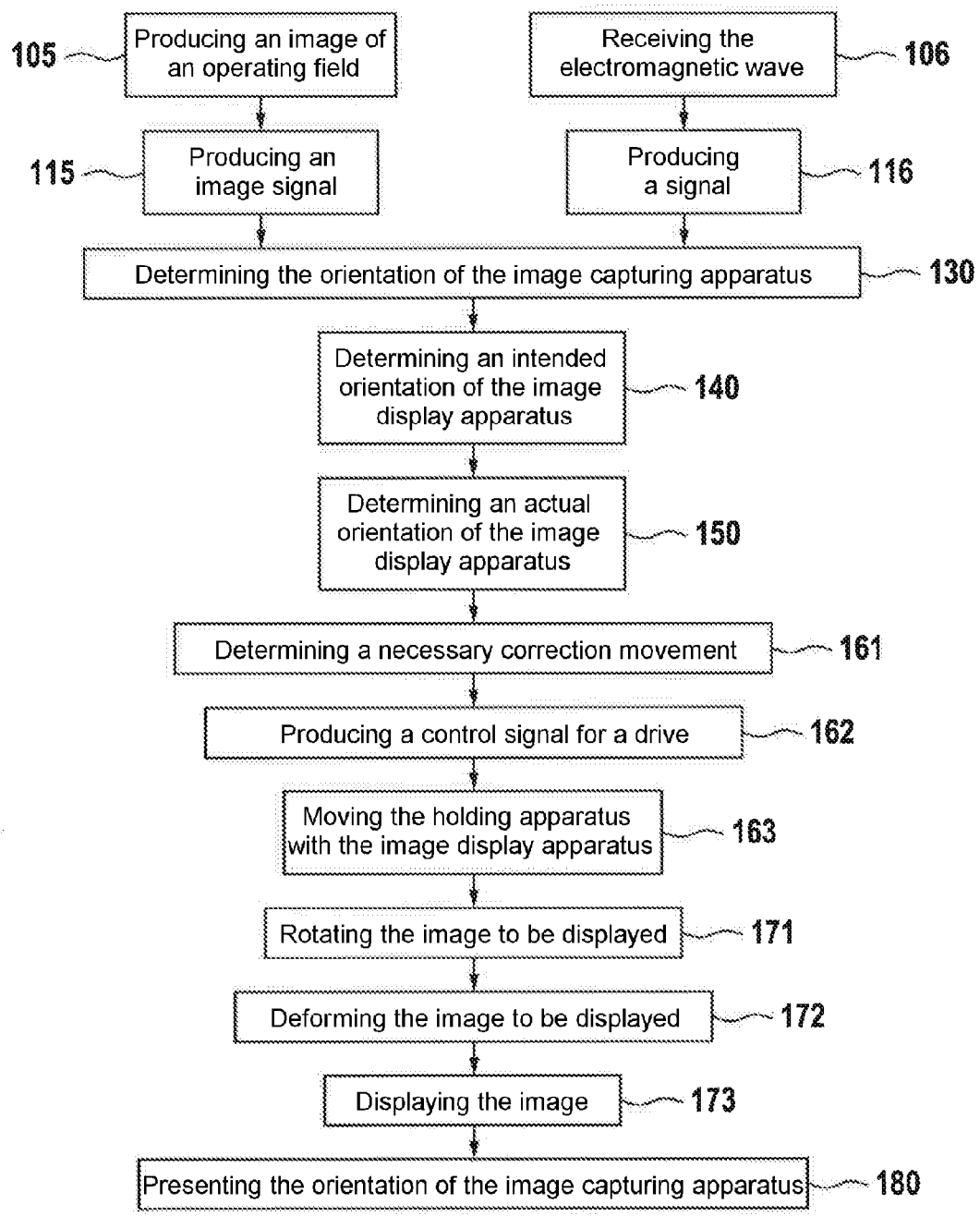
FIG. 13 shows a schematic flowchart of a method for displaying an image.

FIG. 13 shows a schematic flowchart of a further method that is similar to the method presented on the basis of FIG. 12 in a plurality of steps, properties and functions. In particular, steps in which the method shown in FIG. 13 differs from the method presented on the basis of FIG. 12 are described below.

An image of an operating field, in which a proximal end of an image capturing apparatus 20 is also disposed, is produced by a camera 30 in a step 105. An image signal representing the captured image is produced in a step 115, which occurs simultaneously or immediately thereafter.

An electromagnetic wave, which emanates from a transponder or a transmitter 36 in or at an image capturing apparatus, is received in a further step 106, in particular by means of an antenna or any other receiving device 34. A signal representing the amplitude, intensity or power density and/or the polarization and/or a phase of the received electromagnetic wave is produced in a further step 116, which is carried out simultaneously or immediately thereafter. The orientation of the transponder or transmitter 36 and hence of the image capturing apparatus 20 in space can be deduced from the signal.

Steps 105, 115 and steps 106, 116 represent alternatives. A method may comprise steps 105, 115 and/or steps 106, 116.

The orientation of the image capturing apparatus 20 in space is determined in a further step 130 by evaluating the image signal produced in step 115 and/or by evaluating the signal produced in step 116.

The further steps of the method shown in FIG. 13 correspond to the steps already described on the basis of FIG. 12.

Steps 101, 111 and/or steps 102, 112 and/or steps 103, 113, 123 and/or steps 104, 114, 124 from the method presented on the basis of FIG. 12 can be combined with steps 105, 115 and/or with steps 106, 116 from the method presented on the basis of FIG. 13.

LIST OF REFERENCE SIGNS

12 Medical member of staff
14 Medical instrument
16 Cavity in the body of a patient
18 Organ or any other object in the cavity 16 of the patient
20 Endoscope as an image capturing apparatus
22 Distal end of the endoscope 20
24 Proximal end of the endoscope 20
25 Camera that is coupled to the proximal end 24 of the endoscope 20 or integrated into the endoscope 20
26 Structure at the proximal end 24 for identifying the orientation of the endoscope 20
28 Viewing direction of the endoscope 20 and first axis of rotation
29 Edge of the region captured by the endoscope 20
30 Camera for optically capturing the proximal end 24 of the endoscope 20
32 Stand for the camera 30
34 Device for electromagnetically capturing the orientation of the endoscope 20
36 Transponder in or at the endoscope 20
38 Sensor or transponder or transmitter at or in the endoscope 20 (more particularly, sensor for the direction of the gravitational force or of the Earth's magnetic field or of another magnetic or electric field or for an acceleration or a rotation rate sensor)
40 Controller
42 Signal input of the controller 40, coupled to camera 30 or device 34 or sensor 38
47 Signal output of the controller 40, coupled to signal input 74 of the drive device 72 of the arm 70 that is movable in motor-driven fashion
54 Rotation movement of the endoscope 20 about its viewing direction 28 (first rotational degree of freedom of the endoscope 20)
55 Horizontal second axis of rotation, orthogonal to the viewing direction and first axis of rotation 28 and to the third axis of rotation 57
56 Pivot or rotation movement of the endoscope 20 about the second axis of rotation 55 (second rotational degree of freedom of the endoscope 20)
57 Third axis of rotation, orthogonal to the viewing direction and first axis of rotation 28 and to the horizontal second axis of rotation 55
58 Pivot or rotation movement of the endoscope 20 about the third axis of rotation 57 (third rotational degree of freedom of the endoscope 20)
60 Screen as image display apparatus
62 Image display surface of the screen 60
63 Surface normal of the image display surface 62 and first axis of rotation of the screen 60
64 Rotation movement of the screen 60 about the surface normal and first axis of rotation 63 (first rotational degree of freedom of the screen 60)
65 Horizontal second axis of rotation of the screen 60, orthogonal to the first axis of rotation 63
66 Pivot or rotation movement of the endoscope 20 about the second axis of rotation 65 (second rotational degree of freedom of the screen 60)
67 Third axis of rotation of the screen 60, orthogonal to the first axis of rotation 63 and to the second axis of rotation 65
68 Pivot or rotation movement of the endoscope 20 about the third axis of rotation 67 (third rotational degree of freedom of the screen 60)
70 Movable arm as movable holding apparatus with a plurality of degrees of freedom
71 Joint of the movable arm 70
72 Drive device for the movable arm 70
74 Control signal input for the drive device 72
75 Path in a vertical plane, along which the screen 60 is movable
76 Translational movement of the screen 60 along the first path 75 (first translational degree of freedom of the screen 60)
77 Horizontal path, along which the screen 60 is movable
78 Translational movement of the screen 60 along the second path 75 (second translational degree of freedom of the screen 60)
83 First virtual axis of rotation of the image displayed on the screen 60
84 First virtual rotational degree of freedom of the image displayed on the screen 60 (virtual rotation about the first virtual axis of rotation 83)
85 Second virtual axis of rotation of the image displayed on the screen 60, orthogonal to the first virtual axis of rotation 83 and horizontal
86 Second virtual rotational degree of freedom of the image displayed on the screen 60 (virtual rotation about the second virtual axis of rotation 85)
87 Third virtual axis of rotation of the image displayed on the screen 60, orthogonal to the first virtual axis of rotation 83 and to the second virtual axis of rotation 85
88 Third virtual rotational degree of freedom of the image displayed on the screen 60 (virtual rotation about the third virtual axis of rotation 87)
90 Console of a surgical system
91 Input appliance on the console 90
101 Capturing the direction of the gravitational force and producing a sensor signal
102 Capturing the direction of an electric or magnetic field
103 Capturing a linear acceleration
104 Capturing a rotation rate
105 Producing an image signal
106 Receiving the electromagnetic wave
111 Producing a sensor signal
112 Producing a sensor signal
113 Producing a sensor signal
114 Producing a sensor signal
115 Producing an image signal
116 Producing a signal
123 Integrating the sensor signal
124 Integrating the sensor signal 130 Determining the present orientation of the image capturing apparatus 20
140 Determining an intended orientation of the image display apparatus 60
150 Determining an actual orientation of the image display apparatus 60
161 Determining a necessary correction movement
162 Producing a control signal for a drive (72)
163 Moving the holding apparatus 70 with the image display apparatus (60) to the intended orientation
171 Rotating the image to be displayed by the image display apparatus 60
172 Deforming the image to be displayed by the image display apparatus 60
173 Displaying the image on the image display apparatus 60
180 Graphically or numerically presenting the orientation of the image capturing apparatus 20 in space on the image display surface 62

The invention claimed is:

1. A system for holding an image display apparatus for displaying an image captured by means of an image capturing apparatus, comprising:
    a movable holding apparatus for an alterable hold of the image display apparatus;
    a controllable drive device for moving the holding apparatus, comprising a control signal input for receiving a control signal;
    a controller comprising a signal input for receiving a signal that represents an orientation or a change in the orientation of the viewing direction of the image capturing apparatus in space or that facilitates a determination of the orientation or the change in the orientation of the viewing direction of the image capturing apparatus, and comprising a control signal output, couplable to the control signal input of the controllable drive device, for providing a control signal for controlling the controllable drive device,
    wherein the controller is embodied and provided to control the controllable drive device in such a way that, within a predetermined range of possible orientations of the viewing direction of the image capturing apparatus in space, the orientation of the image display apparatus in space is a predetermined function of the orientation of the viewing direction of the image capturing apparatus in space.

2. The system according to claim 1, wherein the controller is embodied to control the drive device in such a way that, within a predetermined angle range, pivoting of the viewing direction of the image capturing apparatus about a first axis causes pivoting of the image display apparatus about a second axis.

3. The system according to claim 1, wherein the controller is embodied to control the drive device in such a way that, in respect of pivoting the viewing direction of the image capturing apparatus about the first axis and pivoting the image display apparatus about the second axis within the predetermined angle range, every angle position of the viewing direction of the image capturing apparatus is associated with an angle position of the image display apparatus.

4. The system according to claim 2, wherein the controller is further embodied to control the drive device in such a way that pivoting of the viewing direction of the image capturing apparatus about the first axis further causes a movement of the image display apparatus along a path.

5. The system according to claim 1, wherein
    the signal input of the controller is further configured to receive a signal that represents a position or a change in the position of the image capturing apparatus or that facilitates a determination of the position or the change in the position of the image capturing apparatus,
    the controller is further embodied and provided to control the controllable drive device in such a way that, within a predetermined range of possible positions of the image capturing apparatus, the position of the image display apparatus is a predetermined function of the position of the image capturing apparatus.

6. The system according to claim 1, wherein the signal input of the controller is embodied to receive from a sensor a signal or a signal that has been integrated over time.

7. The system according to claim 1, wherein
    the signal input of the controller is embodied to receive an image signal from a camera for capturing an operating field,
    the controller is embodied and provided to determine the orientation of the image capturing apparatus by evaluating an image signal received at the signal input.

8. The system according to claim 1, wherein
    the signal input of the controller is embodied to receive a signal from a receiver for electromagnetic waves which emanate from the image capturing apparatus,
    the controller is embodied and provided to determine the orientation of the image capturing apparatus in space by evaluating the signal received from the receiver.

9. The system according to claim 1, wherein
    the controller is embodied to control the drive device in such a way that, within a predetermined angle range, a rotation of the image capturing apparatus through a first angle about its viewing direction causes a rotation of the image display apparatus through a second angle,
    the second angle is a predetermined fraction of the first angle or a predetermined function of the first angle or a predetermined function of the angle position of the image capturing apparatus.

10. A method for displaying an image captured by means of a movable image capturing apparatus, including the following steps:
    capturing the orientation of the viewing direction of the image capturing apparatus in space by means of a sensor;
    setting the orientation of the image display apparatus in space depending on the orientation of the image capturing apparatus in space.

11. The method according to claim 10, further including the following step:
    presenting the orientation of the image capturing apparatus in space graphically or numerically on an image display surface of the image display apparatus.

12. The method according to claim 10, further including the following step:
    deforming the image presented on the image display surface depending on an orientation in the viewing direction of the image capturing apparatus in space.

* * * * *